(12) United States Patent
Slade

(10) Patent No.: US 6,894,060 B2
(45) Date of Patent: May 17, 2005

(54) METHOD FOR THE TREATMENT OF DERMAL LESIONS CAUSED BY ENVENOMATION

(75) Inventor: Herbert B. Slade, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/820,420

(22) Filed: Mar. 29, 2001

(65) Prior Publication Data

US 2002/0016332 A1 Feb. 7, 2002

Related U.S. Application Data

(60) Provisional application No. 60/193,120, filed on Mar. 30, 2000.

(51) Int. Cl.[7] .............................................. A61K 31/44
(52) U.S. Cl. ...................................................... 514/293
(58) Field of Search ......................................... 514/293

(56) References Cited

U.S. PATENT DOCUMENTS

| | | | |
|---|---|---|---|
| 3,314,941 | A | 4/1967 | Littell et al. |
| 3,917,624 | A | 11/1975 | Abu El-Haj et al. |
| 4,689,338 | A | 8/1987 | Gerster |
| 4,698,348 | A | 10/1987 | Gerster |
| 4,929,624 | A | 5/1990 | Gerster et al. |
| 5,037,986 | A | 8/1991 | Gerster |
| 5,238,944 | A | 8/1993 | Wick et al. |
| 5,266,575 | A | 11/1993 | Gerster |
| 5,268,376 | A | 12/1993 | Gerster |
| 5,346,905 | A | 9/1994 | Gerster |
| 5,352,784 | A | 10/1994 | Nikolaides et al. |
| 5,389,640 | A | 2/1995 | Gerster et al. |
| 5,444,065 | A | 8/1995 | Nikolaides et al. |
| 5,446,153 | A | 8/1995 | Lindstrom et al. |
| 5,482,936 | A | 1/1996 | Lindstrom |
| 5,494,916 | A | 2/1996 | Lindstrom et al. |
| 5,585,612 | A | 12/1996 | Harp, Jr. |
| 5,605,899 | A | 2/1997 | Gerster et al. |
| 5,627,281 | A | 5/1997 | Nikolaides et al. |
| 5,644,063 | A | 7/1997 | Lindstrom et al. |
| 5,648,516 | A | 7/1997 | Nikolaides et al. |
| 5,714,608 | A | 2/1998 | Gerster |
| 5,741,909 | A | 4/1998 | Gerster et al. |
| 5,886,006 | A | 3/1999 | Nikolaides et al. |
| 5,939,090 | A | 8/1999 | Beaurline et al. |
| 5,977,366 | A | 11/1999 | Gerster et al. |
| 6,039,969 | A | 3/2000 | Tomai et al. |
| 6,069,149 | A | 5/2000 | Nanba et al. |
| 6,083,505 | A | 7/2000 | Miller et al. |
| 6,110,929 | A * | 8/2000 | Gerster et al. |
| 6,194,425 | B1 | 2/2001 | Gerster et al. |

FOREIGN PATENT DOCUMENTS

| | | |
|---|---|---|
| EP | 0 894 797 A1 | 2/1998 |
| JP | 9-208584 | 8/1997 |
| WO | WO 93/09119 | 5/1993 |
| WO | WO 97/48704 | 12/1997 |
| WO | WO 98/17279 | * 4/1998 |
| WO | WO 00/09506 | 2/2000 |
| WO | WO 00/40228 | 7/2000 |
| WO | WO 00/76505 | 12/2000 |
| WO | WO 00/76518 | 12/2000 |

OTHER PUBLICATIONS

Leynadier et al., Journal of Allergy and Clinical Immunology, 1997; 99(6 pt 1): 851–853.*
Bitterman–Deutsch et al., HAREFUAH, 1990; 119(5–6):137–139.*
Mosbech et al., Ugeskrift for Laeger, 1991;153(44):3067–3071.*
Binder, Medical Toxicology and Adverse Drug Experience, 1989; 4(3):163–173.*
Auerbach et al., Journal of Emergency Medicine, 1987;5(6):487–491.*
Wozniak, et al, "The Amination of 3–nitro–1, 5–naphthyridines by Liquid Ammonia/Potassium Permanganate[1,2], A New and Convenient Amination Method." *Journal of the Royal Netherlands Chemical Society*, 102, pp 511–513, Dec. 12, 1983.
Brennan, et al, "Automated Bioassay of Interferons in Micro–test Plates", *Biotechniqes*, Jun./Jul., 78, 1983.
Testerman, et al, "Cytokine Induction by the Immunomodulators Imiquimod and S–27609", *Journal of Leukocyte Biology*, vol. 58, pp. 365–372, Sep. 1995.
Bachman, et al, "Synthesis of Substituted Quinolylamines. Derivatives of 4–Amino–7–Chloroquinoline", *J. Org. Chem*, 15, pp 1278–1284 (1950).
Jain, et al, "Chemical and Pharmacological Investigations of Some ω–Substituted Alkylamino–3–aminopyridines", *J. Med. Chem.*, 11, pp 87–92 (1968).
Baranov, et al., *Chem. Abs.* 85, 94371, (1976).
Berényi, et al, "Ring Transformation of Condensed Dihydro–as–triazines", *J. Heterocyclic Chem.*, 18, pp 1537–1540 (1981).
G.S. Wasserman and P.C. Anderson, "Loxoscelism and Necrotic Arachnidism," *J. Toxicol.–Clin. Toxicol.*, 21(4&5), 451–472 (1983–84).
"Dapsone (diaminodiphenylsulphone, DDS)," *Clinical Toxicology Review*, vol. 21, No. 9, pp. 1–3 (Jun. 1999).

(Continued)

Primary Examiner—Sreeni Padmanabhan
Assistant Examiner—Sen-ming Hui
(74) Attorney, Agent, or Firm—Christopher D. Gram; Robert W. Sprague

(57) ABSTRACT

A method of treating dermal lesions caused by envenomation comprising applying a therapeutically effective amount of an immune response modifier compound selected from the group consisting of imidazoquinoline amines, imidazopyridine amines, 6,7-fused cycloalkylimidazopyridine amines, imidazonaphthyridine amines, tetrahydroimidazonaphthyridine amines, oxazolopyridine amines, oxazoloquinoline amines, thiazolopyridine amines, thiazoloquinoline amines and 1,2-bridged imidazoquinoline amines to the site of the lesion is disclosed.

14 Claims, No Drawings

OTHER PUBLICATIONS

Merigian KS, Blaho K. Envenomation from the brown recluse spider: Review of mechanism and treatment options. American Journal of Therapeutics 1996; 3: 724–734.

Borkan J, Gross E, Lubin Y, Oryan I. An outbreak of venomous spider bites in a citrus grove. American Journal of Tropical Medicine & Hygiene 1995; 52: 228–230.

Beutner KR, Spruance SL, Hougham AJ, Fox TL, Owens ML, Douglas JM, Jr. Treatment of genital warts with an immune–response modifier (imiquimod). J.Am.Acad.Dermatol. 1998; 38: 230–239.

Gendron BP. Loxosceles reclusa envenomation. American Journal of Emergency Medicine 1990; 8: 51–54.

Stack LB. Lacrodectus mactans. N.Engl.J.Med. 1997; 336: 1649.

Wilson DC, King LE, Jr. Spiders and spider bites. Dermatologic Clinics 1990; 8: 277–286.

Wright SW, Wrenn KD, Murray L, Seger D. Clinical presentation and outcome of brown recluse spider bite. Annals of Emergency Medicine 1997; 30: 28–32.

Cole III, Wesley RE, King JL. Brown recluse spider envenomation of the eyelid: An animal model. Ophthalmic Plastic & Reconstructive Surgery 1995; 11: 153–164.

Broughton IIG. Management of the brown recluse spider bite to the glans penis. Military Medicine 1996; 161: 627–629.

Beilman GJ, Winslow CL, Teslow TW. Experimental brown spider bite in the guinea pig: Results of treatment with dapsone or hyperbaric oxygen. Journal of Wilderness Medicine 1994; 5: 287–294.

Maynor ML, Moon RE, Klitzman B, Fracica PJ, Canada A. Brown recluse spider envenomation: A prospective trial of hyperbaric oxygen therapy. Academic Emergency Medicine 1997; 4: 184–192.

Hobbs GD, Anderson AR, Greene TJ, Yealy DM. Comparison of hyperbaric oxygen and dapsone therapy for Loxosceles envenomation. Academic Emergency Medicine 1996; 3: 758–761.

Rees RS, Altenbern DP, Lynch JB, King LE, Jr. Brown recluse spider bites. A comparison of early surgical excision versus dapsone and delayed surgical excision. Annals of Surgery 1985; 202: 659–663.

Ottonello L, Dapino P, Scirocco MC, Balbi A, Bevilacqua M, Dallegri F. Sulphonamides as anti–inflammatory agents: old drugs for new therapeutic strategies in neutrophilic inflammation? Clinical Science 1995; 88: 331–336.

Debol SM, Herron MJ, Nelson RD. Anti–inflammatory action of dapsone: inhibition of neutrophil adherence is associated with inhibition of chemoattractant–induced signal transduction. Journal of Leukocyte Biology 1997; 62: 827–836.

Booth SA, Moody CE, Dahl MV, Herron MJ, Nelson RD. Dapsone suppresses integrin–mediated neutrophil adherence function. Journal of Investigative Dermatology 1992; 98: 135–140.

Phillips S, Kohn M, Baker D, et al. Therapy of brown spider envenomation: A controlled trial of hyperbaric oxygen, dapsone, and cyproheptadine. Annals of Emergency Medicine 1995; 25: 363–368.

Majeski JA, Stinnett JD, Alexander JW, Durst GG, Sr. Action of venom from the brown recluse spider (*Loxosceles reclusa*) on human neutrophils. Toxicon 1977; 15: 423–427.

Luger TA, Schwarz T. Evidence for an epidermal cytokine network. [Review] [54 refs]. Journal of Investigative Dermatology 1990; 95: 100S–104S.

Patel KD, Modur V, Zimmerman GA, Prescott SM, McIntyre TM. The necrotic venom of the brown recluse spider induces dysregulated endothelial cell–dependent neutrophil activation. Differential induction of GM–CSF, IL–8, and E–selectin expression. Journal of Clinical Investigation 1994; 94: 631–642.

Gomez HF, Miller MJ, Trachy JW, Marks RM, Warren JS. Intradermal anti–loxosceles Fab fragments attenuate dermonecrotic arachnidism. Academic Emergency Medicine 1999; 6: 1195–1202.

Gibson SJ, Imbertson LM, Wagner TL, et al. Cellular requirements for cytokine production in response to the immunomodulators imiquimod and S–27609. Journal of Interferon & Cytokine Research 1995; 15: 537–545.

Miller R, Birmachu W, Gerster J, et al. Imiquimod: cytokine induction and antiviral activity. Antiviral News 1995; 3: 111–113.

Tomai MA, Birmachu W, Case MT, et al. Imiquimod: in vivo and in vitro characteristics and toxicology. In: Aly R, Beutner KR, Maibach H, eds. Cutaneous infection and therapy, New York: Marcel Dekkar, Inc., 1997: 405–415.

Sams HH, Dunnick CA, Smith ML, King LE, Jr. Necrotic arachnidism. J Am Acad Dermatol 2001; 44:561–73.

Smith, CW, Micks DW. The role of polymorphonuclear leukocytes in the lesion caused by the venom of the brown spider, *Loxosceles reclusa*. Laboratory Investigation 1970; 22:90–3.

\* cited by examiner

METHOD FOR THE TREATMENT OF DERMAL LESIONS CAUSED BY ENVENOMATION

This application claims benefit of Provisional Application No. 60/193,120, filed Mar. 30, 2000.

FIELD OF THE INVENTION

The present invention relates to methods for treating dermal lesions caused by envenomation. In particular the present invention relates to a method of treating dermal lesions caused by envenomation comprising applying a therapeutically effective amount of an immune response modifier compound selected from the group consisting of imidazoquinoline amines, imidazopyridine amines, 6,7-fused cycloalkylimidazopyridine amines, imidazonaphthyridine amines, tetrahydroimidazonaphthyridine amines, oxazolopyridine amines, oxazoloquinoline amines, thiazolopyridine amines, thiazoloquinoline amines and 1,2-bridged imidazoquinoline amines to the site of the lesion. The present invention also provides a method of preventing dermonecrosis caused by envenomation comprising applying a therapeutically effective amount of an immune response modifier compound selected from the group consisting of imidazoquinoline amines, imidazopyridine amines, 6,7-fused cycloalkylimidazopyridine amines, imidazonaphthyridine amines, tetrahydroimidazonaphthyridine amines, oxazolopyridine amines, oxazoloquinoline amines, thiazolopyridine amines, thiazoloquinoline amines and 1,2-bridged imidazoquinoline amines to the site of the envenomation.

BACKGROUND OF THE INVENTION

Many imidazoquinoline amine, imidazopyridine amine, 6,7-fused cycloalkylimidazopyridine amine, imidazonaphthyridine amine, tetrahydroimidazonaphthyridine amine, oxazolopyridine amine, oxazoloquinoline amine, thiazolopyridine amine, thiazoloquinoline amine and 1,2-bridged imidazoquinoline amine immune response modifiers are known. These compounds are hereinafter sometimes referred to as immune response modifying compounds (IRMs). Such compounds, methods for preparing them, formulations containing them and methods of using them are disclosed in, for example, U.S. Pat. Nos. 4,689,338; 5,389,640; 5,268,376; 4,929,624; 5,266,575; 5,352,784; 5,494,916; 5,482,936; 5,395,937; 5,238,944; 5,175,296; 5,693,811; 5,741,908; 5,756,747; 5,939,090; 6,110,929; 4,988,815; 5,376,076; 6,083,505; 6,039,969; and PCT Publications WO 99/29693, WO 00/40228, WO 00/76505, WO 00/76518 and WO 00/76518.

The IRM compounds have demonstrated antiviral and antitumor activity. The antiviral and antitumor activity is not direct but is believed to result from their ability to stimulate an innate immune response. In cultures of human peripheral blood mononuclear cells, members of this class of compounds have been shown to stimulate the production and release of a variety of cytokines and chemokines including interferon-α, tumor necrosis factor-α, interleukin-1 (IL-1), IL-1 receptor antagonist, IL-6, IL-8, IL-12, monocyte chemotactic protein-1 (MCP-1) and macrophage inflammatory protein (MIP-1α).

In addition to stimulating an innate immune response, the IRM compounds have been found to mediate the acquired immune response. In human peripheral blood mononuclear cell cultures, members of this class of compounds have been shown to induce the production of the T helper type 1 (TH1) cytokine interferon-γ and to inhibit the production of T helper type 2 (TH2) cytokines IL-4 and IL-5.

One of these IRM compounds, known as imiquimod (1-(2-methylpropyl)-1H-imidazo[4,5-c]quinolin-4-amine), has been commercialized in a topical formulation, Aldara™ cream, for the treatment of anogenital warts associated with human papillomavirus. Imiquimod is also being evaluated in clinical trials for use in treating superficial basal cell carcinoma and actinic keratosis.

Another of these IRM compounds, known as resiquimod (4-amino-2-ethoxymethyl-α,α-dimethyl-1H-imidazo[4,5-c] clinical trials for use in preventing genital herpes recurrences.

There are numerous venomous flora and fauna in the world, some of which possess venom that causes significant medical problems when a human or an animal is exposed to the venom. Envenomation by such a plant or animal can cause both systemic and local reactions. Examples of local reactions include edema, erythema, induration, necrotic ulcers, pain, pruritis, and vesicles. The severity of the reaction is dependent on a variety of factors including the source of the venom (e.g. *Loxosceles* spider, box jellyfish, fire ant), the amount of venom injected, the location of the bite or sting (e.g. arm, thigh), and prior exposure to the venom. A variety of treatments have been used including analgesics, antibiotics, antivenoms, corticosteroids, Dapsone, and hyperbaric oxygen. In those instances where the initial dermal lesion progresses to dermonecrosis, surgical intervention is often necessary. There is a continuing need for new treatments and in particular for treatments that will prevent dermonecrosis.

SUMMARY OF THE INVENTION

The present invention relates to a method of treating dermal lesions caused by envenomation comprising applying a therapeutically effective amount of an immune response modifier compound selected from the group consisting of imidazoquinoline amines, imidazopyridine amines, 6,7-fused cycloalkylimidazopyridine amines, imidazonaphthyridine amines, tetrahydroimidazonaphthyridine amines, oxazolopyridine amines, oxazoloquinoline amines, thiazolopyridine amines, thiazoloquinoline amines and 1,2-bridged imidazoquinoline amines to the site of the lesion.

The present invention also provides a method of preventing dermonecrosis caused by envenomation comprising applying a therapeutically effective amount of an immune response modifier compound selected from the group consisting of imidazoquinoline amines, imidazopyridine amines, 6,7-fused cycloalkylimidazopyridine amines, imidazonaphthyridine amines, tetrahydroimidazonaphthyridine amines, oxazolopyridine amines, oxazoloquinoline amines, thiazolopyridine amines, thiazoloquinoline amines and 1,2-bridged imidazoquinoline amines to the site of the envenomation.

DETAILED DESCRIPTION OF THE INVENTION

As used herein the term "envenomation" means injection of a poisonous material (venom) by sting, spine, fang, tooth, or other venom delivery apparatus.

Immune response modifier (IRM) compounds that are useful in practicing the methods of the present invention are selected from the group consisting of imidazoquinoline amines, imidazopyridine amines, 6,7-fused cycloalkylimidazopyridine amines, imidazonaphthyridine amines, tetrahydroimidazonaphthyridine amines, oxazolopyridine amines, oxazoloquinoline amines, thiazolopyridine amines, thiazoloquinoline amines and 1,2-bridged imidazoquinoline amines. Such compounds and methods for preparing them are disclosed in, for example, U.S. Pat. Nos. 4,689,338; 5,389,640; 5,268,376; 4,929,624; 5,266,575; 5,352,784; 5,494,916; 5,482,936; 5,395,937; 5,175,296; 5,693,811; 5,741,908; 5,756,747; 6,110,929; 4,988,815; 5,376,076; 6,083,505; 6,039,969; and International Publications WO 99/29693; WO 00/76505; WO 00/76518 and WO 00/76518. The entire disclosure of each of these patents and patent applications is incorporated herein by reference.

Preferred IRM compounds for use in the practice of the methods of the invention include compounds of Formula I $$\text{Formula I}$$

wherein
$R_1$ is selected from the group consisting of S and $NR_3$,
$R_2$ is selected from the group consisting of hydrogen, straight and branched chain alkyl containing one to six carbon atoms, and alkoxyalkyl wherein the alkoxy moiety contains one to four carbon atoms and the alkyl moiety contains one to four carbon atoms; and
$R_3$ is selected from the group consisting of straight and branched chain alkyl containing one to six carbon atoms and straight and branched chain hydroxy alkyl containing one to six carbon atoms; or a pharmaceutically acceptable salt thereof.

Preferred $R_2$ groups include hydrogen, methyl, ethyl, propyl, butyl, and ethoxymethyl.

Preferred $R_3$ groups include 2-methylpropyl and 2-hydroxy-2-methylpropyl.

Particularly preferred IRM compounds include 4-amino-2-ethoxymethyl-α,α-dimethyl-1H-imidazo[4,5-c]quinoline-1-ethanol (resiquimod), 1-(2-methylpropyl)-1H-imidazo[4,5-c]quinolin-4-amine (imiquimod), 2-methylthiazolo[4,5-c]quinolin-4-amine, 2-ethylthiazolo[4,5-c]quinolin-4-amine, 2-propylthiazolo[4,5-c]quinolin-4-amine and 2-butylthiazolo[4,5-c]quinolin-4-amine.

In the method of the invention a therapeutically effective amount of the IRM compound is applied. The term "therapeutically effective amount" means an amount sufficient to induce a therapeutic effect such as the amelioration of symptoms (e.g. pain, erythema diminution of lesions,) or the prevention of dermonecrosis. The specific amount that will constitute a therapeutically effective amount will vary according to factors readily determined by those skilled in the art including the activity of the particular IRM compound being used, the particular formulation being administered, the duration of the administration and the frequency of the administration. Generally from about 1 µg to about 125 mg, preferably from about 10 µg to about 25 mg, of the IRM compound is applied to the dermal lesion.

Any conventional dosage form suitable for topical application may be used including creams, gels, lotions, ointments, sprays and transdermal patches. Preferred formulations include creams and gels. Suitable formulations are disclosed, for example, in U.S. Pat. Nos. 5,238,944 and 5,939,090 and International Publication WO 00/40228, the disclosures of which are incorporated by reference herein.

The frequency and duration of administration can vary as needed for amelioration of symptoms and/or prevention of dermonecrosis. Treatment regimens may include administration from twice per day to once per week, preferably two to three times per week, for at least one week, preferably for two to three weeks.

There are many venomous creatures whose bite or sting causes local reactions in humans. Examples of such creatures include, for example, arthropods such as arachnids (e.g., scorpions, spiders) and insects of the order Hymenoptera (e.g., bees, wasps, ants), and marine animals such as jellyfish, stone fish, stingrays, and blue ringed octopus. The venom of some species is known to cause dermal lesions that can progress to dermonecrosis. Examples of such species include *Loxosceles* spiders (*L. reclusa, L. deserta, L. laeta*), hobo spiders (*Tegenaria* spp), yellow sac spiders (*Cheiracanthium* spp.), fire ants (*Solenopsis invicta*), and jellyfish (*Chironex fleckeri, Carybdea alata, Cassiopea andromeda, Aurelia aurita*).

Venoms are frequently complex mixtures of a variety of substances. Substances that have been identified include enzymes e.g. phospholipases, hyaluronidases, cholinesterases; alkaloids e.g. methyl-N-piperidine; proteins e.g. melittin; and peptides. The particular constituents will depend on the source of the venom. When envenomation occurs a number of different types of epithelial and endothelial cells are exposed to the venom. These cells are capable of synthesizing and releasing a wide variety of chemokines and cytokines in response to a variety of stimuli. For example, it has been shown in vitro that *Loxosceles deserta* venom induces endothelial and epithelial cells to secrete both α and β chemokines. The release of chemokines and cytokines triggers additional events such as the attraction of neutrophils to the site of envenomation. While some of the local skin reactions that are manifested as a result of envenomation such as edema and erythema are caused directly by constituents of the venom due to the hemolytic action of various enzymes, it has been hypothesized that dermonecrosis may be due to an immune response.

While not wishing to be bound by theory, it is believed that effects of the IRM compound overwhelm the local physiological effects of the venom. This may occur by modifying the qualitative properties of the local soluble mediators of inflammation such that signaling for neutrophil activation and degranulation is inhibited. In addition, the early aggregation of neutrophils in dermal blood vessels may be diffused by IRM compound induced cytokines by stimulating the migration of neutrophils out of local vasculature and into surrounding tissue. Thus, if activated neutrophils are no longer aggregated in the discrete focal area of the site of envenomation, the amount of central necrosis may be inhibited. In essence, the venom induced "immune dysregulation" may be overcome by the immune stimulation provided by the IRM compound.

EXAMPLE

Treatment of *Loxosceles reclusa* Envenomation with Imiquimod 5% Cream

Background

A privatized correctional facility in Texas experienced a cluster of spider bite cases due to *L. reclusa* shortly following the receipt of a shipment of used mattresses from a local county jail. Spiders may have inhabited the mattresses when they were stored for several weeks in a dark shed out behind the facility. Following the first several cases, fumigation with a synthetic pyrethroid (PT 1200, resmethrin) was performed. While this agent is considered effective against *L. reclusa*, the spiders must generally be contacted directly, and unhatched eggs are less susceptible.

The diagnosis of loxoscelism in these cases was made by exclusion. No spiders were recovered despite the use of glue traps, although in one case, a "brown spider" dropped from the ceiling of a shower onto the breast of a female patient, who brushed the spider away after sustaining a bite. The following aspects of these cases favor a diagnosis of *L. reclusa* envenomation: the spider is endemic to the area; the bites occurred mostly at night and were characterized by lack of immediate pain. Blanching and cyanosis slowly developed at the central core, with spreading erythema and progression to dermonecrosis. Other insects are known to inflict bites with similar clinical findings but can be excluded on the grounds that they are not found in Texas (various tarantulas, Australian funnel-web spiders (*Atrax* spp.), "hobo spiders" (*Tegeneria* spp.); they form characteristic webs not found in the facility (yellow sac spiders (*Chiracanthium* spp.), black-and-yellow orb weavers (*Argiope* spp.); or they bite during the day ("jumping spider" (*Phidippus audax*)). *Phidippus* species are very aggressive and bite commonly, but they inflict only slightly painful bites resulting in erythematous papules or small urticarial wheals. The only alternative suspect is *Latrodectus mactans* ("Southern black widow"). This spider is shy in behavior, similar to *L. reclusa*, and bites often go unnoticed until a red papule progresses to a larger halo or target lesion up to 2 cm in diameter. Unlike the *L. reclusa* bite however, skin manifestations are minimal. Victims are more likely to experience muscle spasms and cramping within hours of envenomation, together with weakness of the legs and tightness of the chest. These clinical findings were absent in the cases reported here.

Methods

Patients were seen in the facility clinic on the day they complained of a painful lesion. Most patients related a history of discovering the lesion upon awakening in the morning. The treatment of the first 12 consecutive cases, occurring over a 5 month period, consisted of a single intramuscular dose of ceftriaxone 1 gm and oral dicloxicillin 500 mg bid×10 days, plus either topical triamcinolone 0.1% applied bid, topical papain-urea-chlorophyllin copper complex sodium debriding-healing ointment (Panafil™) applied daily, or daily topical becaplermin (rh-PDGF-BB) 0.01% gel (Regranex™). Where necessary and appropriate, patients were transported to the local University Medical Center for surgical debridement of necrotic lesions.

A consecutive series of 7 bites on 5 patients were treated with imiquimod 5% cream (available under the tradename ALDARA from 3M Pharmaceuticals, St. Paul, Minn., USA) applied by the clinic staff, three times per week (typically Monday, Wednesday and Friday) for two weeks. Sufficient cream was used to cover the area of erythema, rubbing the cream gently until it "vanished" as per labeled instructions. In addition, a single intramuscular dose of ceftriaxone 1 gm was given together with oral dicloxicillin, 500 mg bid for 10 days. Patients were re-examined by a physician at 7, 14 and 28 days following initiation of therapy.

Results

The first 12 patients, managed using conventional therapy, presented with tender to painful lesions consisting of a central core of induration and blanching, surrounded by 3–8 cm of erythema. Among these, 7 progressed to tissue necrosis within 1 week after the bite, all of whom were referred for surgical debridement. One patient developed a healing contracture of the forearm which necessitated surgical release. Healing occurred by secondary intention over several months following the bites.

Seven consecutive bites occurring in 5 patients were treated with imiquimod. These cases are summarized in the Table below. Presenting signs and symptoms were consistent with those recorded for patients treated by conventional means. Tenderness or pain, with erythema, characteristic blanching and firm induration were present in every case. In one case (L.S.), punctuate marks were noted at the center of the indurated area. Pain relief was reported by all patients within 1–2 days following the first dose of imiquimod. Marked improvement in both induration and erythema was noted by day 7, with full resolution in all but one case by day 14. In patient Y.C., erythema was noted to be cleared at the day 7 visit but developed again by day 14. The reappearance of erythema is presumed to be secondary to imiquimod Patients C.R. and L.S. each sustained two bites. In the case of L.S., the first bite was resolved 9 days after it occurred. The second bite occurred 16 days after the first bite and resolved completely, with treatment, by the 5th day. The difference in clinical course may have been due to differences in the age of the spider, the sex of the spider (females inject greater volumes of venom), or an acquired immunity following the first bite. Necrosis did not develop in any of the imiquimod treated cases. No residual scarring or pigmentation changes were noted at the day 28 follow-up visit.

The probability of observing 0 out of 7 consecutive cases with no necrosis, given the underlying historical rate of 7/12 (0.583), is quite low based on a binomial probability distribution (p=0.002) or a Chi-square analysis (p=0.01).

Summary of Cases

| Patient/Age/Sex | Bite Location | Presentation | 7 Day Follow-up | 14 Day Follow-up |
|---|---|---|---|---|
| R. M/39 y/M | Right calf | 1.5 cm induration 9 cm erythema Painful | 0.5 cm induration No erythema No pain or tenderness | Completely healed |
| R. H/45 y/M | Right calf | 1.3 cm induration 10 cm erythema Very painful | 1.25 cm firm induration 5 cm induration Non-tender | Completely healed |
| L. S./28 y/F | Right thigh | 1.5 cm induration 7.5 × 11 cm erythema Tender | 2.5 cm central core No erythema No pain or tenderness | Completely healed |
| L. S./28 y/F | Left buttock | 1.0 cm induration Erythema Painful | Completely healed | |
| C. R./35 y/F | Left thigh | 1.0 cm central core 6.0 cm erythema Painful | 0.5 cm central core 2.0 cm erythema | Completely healed |
| C. R./35 y/F | Right breast | 1.2 cm central core 3.0 cm erythema Painful | 1.0 cm central core No erythema | Completely healed |
| Y. C./35 y/F | Right calf | 1.8 cm central core 1.2 cm erythema Painful | 0.75 cm ulcer No erythema Decreased pain | Ulcer healed Erythema present (Erythema resolved by d28) |

What is claimed is:

1. A method of treating dermal lesions caused by venom-induced immune dysregulation, the method comprising applying a therapeutically effective amount of an immune response modifier compound to the site of the lesion, wherein the site of the lesion comprises a spider bite, and wherein the immune response modifier compound is a compound of Formula I

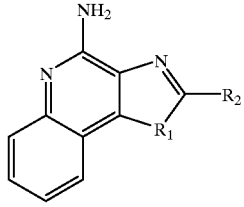

wherein
R₁ is selected from the group consisting of S and NR₃,
R₂ is selected from the group consisting of hydrogen, straight and branched chain alkyl containing one to six carbon atoms, and alkoxyalkyl wherein the alkoxy modifier contains one to four carbon atoms and the alkyl moiety contains one to four carbon atoms; and
R₃ is selected from the group consisting of straight and branched chain alkyl containing one to six carbon atoms and straight or branched chain hydroxy alkyl containing one to six carbon atoms; or a pharmaceutically acceptable salt thereof.

2. The method of claim 1 wherein R₁ is NR₃.
3. The method of claim 1 wherein R₁ is S.
4. The method of claim 1 wherein R₂ is selected from the group consisting of hydrogen, methyl, ethyl, propyl, butyl, and ethoxymethyl.
5. The method of claim 1 wherein R₃ is selected from the group consisting of 2-methylpropyl and 2-hydroxy-2-methylpropyl.
6. The method of claim 1 wherein the IRM compound is selected from the group consisting of 4-amino-2-ethoxymethyl-α,α-dimethyl-1H-imidazo[4,5-c]quinoline-1-ethanol, 1-(2-methylpropyl)-1H-imidazo[4,5-c]quinolin-4-amine, 2-methylthiazolo[4,5-c]quinolin-4-amine, 2-ethylthiazolo[4,5-c]quinolin-4-amine, 2-propylthiazolo[4,5-c]quinolin-4-amine and 2-butylthiazolo[4,5-c]quinolin-4-amine.
7. The method of claim 1 wherein the immune response modifier compound is applied via a cream or a gel.
8. A method of inhibiting dormonecrosis caused by venom-induced immune dysregulation, the method comprising applying a therapeutically effective amount of an immune response modifier compound to the site of the venom-induced immune dysregulation, wherein the site of the venom-induced immune dysregulation comprises a spider bite, and wherein the immune response modifier compound is a compound of Formula I

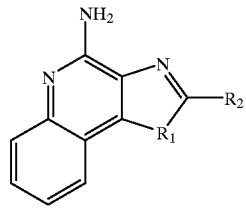

wherein
R₁ is selected from the group consisting of S and NR₃,
R₂ is selected from the group consisting of hydrogen, straight and branched chain alkyl containing one to six carbon atoms, and alkoxyalkyl wherein the alkoxy moiety contains one to four carbon atoms and the alkyl moiety contains one to four carbon atoms; and
R₃ is selected from the group consisting of straight and branched chain alkyl containing one to six carbon atom and straight or branched chain hydroxy alkyl containing one to six carbon atoms; or a pharmaceutically acceptable salt thereof.

9. The method of claim 8 wherein R₁ is NR₃.
10. The method of claim 8 wherein R₁ is S.
11. The method of claim 8 wherein R₂ is selected from the group consisting of hydrogen, methyl, ethyl, propyl, butyl, and ethoxymethyl.
12. The method of claim 8 wherein R₃ is selected from the group consisting of 2-methylpropyl and 2-hydroxy-2-2methylpropyl.
13. The method of claim 8 wherein the IRM compound is selected from the group consisting of 4-amino-2-ethoxymethyl-α,α-dimethyl-1H-imidazo[4,5-c]quinoline-1-ethanol, 1-(2-methylpropyl)-1H-imidazo[4,5-c]quinolin-4-amine, 2-methylthiazolo[4,5-c]quinolin-4-amine, 2-ethylthiazolo[4,5-c]quinolin-4-amine, 2-propylthiazolo[4,5-c]quinolin-4-amine and 2-butylthiazolo[4,5-c]quinolin-4-amine.
14. The method of claim 8 wherein the immune response modifier compound is applied via a cream or a gel.

* * * * *

UNITED STATES PATENT AND TRADEMARK OFFICE
CERTIFICATE OF CORRECTION

PATENT NO. : 6,894,060 B2
DATED : May 17, 2005
INVENTOR(S) : Slade, Herbert B.

It is certified that error appears in the above-identified patent and that said Letters Patent is hereby corrected as shown below:

Column 2,
Line 12, after "[4,5-c]" insert -- quinoline-1-ethanol), is being evaluated in --.

Column 7,
Line 19, delete the word "modifier" and insert in place thereof -- moiety --.
Line 36, delete "α-dimiethyl" and insert in place thereof -- α-dimethyl --.
Line 44, delete the word "dormonecrosis" and insert in place thereof
-- dermonecrosis --.

Column 8,
Line 25, delete the word "atom" and insert in place thereof -- atoms --.
Line 37, delete "2methylpropyl" and insert in place thereof -- methylpropyl --.

Signed and Sealed this

Thirtieth Day of August, 2005

JON W. DUDAS
*Director of the United States Patent and Trademark Office*